(12) United States Patent
Altaba

(10) Patent No.: US 6,238,876 B1
(45) Date of Patent: May 29, 2001

(54) METHODS AND MATERIALS FOR THE DIAGNOSIS AND TREATMENT OF SPORADIC BASAL CELL CARCINOMA

(75) Inventor: Ariel Ruiz i Altaba, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/102,491

(22) Filed: Jun. 22, 1998

Related U.S. Application Data

(60) Provisional application No. 60/050,286, filed on Jun. 20, 1997.

(51) Int. Cl.[7] ................ G01N 33/53; G01N 33/574; C07K 14/47; C12N 5/08
(52) U.S. Cl. .................. 435/7.23; 435/7.2; 435/7.1; 435/70.3; 435/371; 436/64; 530/350; 530/828; 536/23.5
(58) Field of Search ............... 435/7.23, 7.2, 435/7.1, 70.3, 371; 436/64; 530/350, 828; 536/23.5

(56) References Cited

PUBLICATIONS

Ackerman et al., *Neoplasms with follicular differentiation.* Phildephia: Lea and Febinger. Phildephia: Lea and Febinger (1993).
Alexandre et al., *Genes and Dev.* 10, 2003–2013 (1996).
Belloni et al., *Nature Genetics* 14, 353–356 (1996).
Blessing et al., *Genes Dev.* 7, 204–215 (1993).
Bitgood et al., *Dev. Biol.* 172, 126–138 (1996).
Byrne et al., *Development* 120, 2369–2383 (1994).
Cerroni et al., *. J Cutan Pathol* 21, 398–403 (1994).
Chen et al., *Cell* 87, 553–563 (1996).
Chiang et al., *Nature* 383, 407–413 (1996).
Concordet et al., *Development* 122, 2835–2846 (1996).
Cotsarelis et al., *Cell* 61, 1329–1337 (1990).
Domínguez et al., *Science* 272, 1621–1625 (1996).
Echelard et al.,.*Cell* 75, 1417–1430 (1993).
Ekker, et al., *Development* 121, 2337–2347 (1995).
Elder, D. Ed. in chief. *Lever's Histopatology of the Skin.* 8th Edition. Philadelphia, Lippincott–Raven (1997).
Epstein et al.,*Development* 122, 2885–2894 (1996).
Ericson et al., *Cell* 87, 661–673 (1996).
Forbes et al., *Development Supplement* 115–124 (1993).
Fuller et al., *Mutation Research* 276, 299–306 (1992).
Gailani et al., *Nature Genet.* 14, 78–81 (1996).
Goodrich et al., *Genes Dev.* 10, 301–312 (1996).
Grimwood et al., .*Society for Invest. Derm.* 86, 191–194 (1986).
Hahn et al., *Cell* 85, 841–851 (1996).
Hammerschmidt et al., *Genes and Dev.* 10, 647–658 (1996).
Hepker et al., *Development* 124, 549–558 (1997).
Hui et al., *Developmental Biology* 162, 402–413 (1994).
Hynes et al., *Neuron* 15, 35–34 (1995).
Iseki et al., *Biochem. Biophys. Res. Commun.* 218, 688–693 (1996).
Johnson et al., *cience* 272, 1668–1671 (1996).
Kelsey–Motzny et al., *Mechanisms of Development* 52, 137–150 (1995).
Kinzler et al., *Mol. Cell Biol.* 10, 634–642 (1990).
Kinzler et al., *Science* 236, 70–73 (1987).
Krauss et al., *.Cell* 75, 1431–1444 (1993).
Lai et al., *Development* 121, 2349–2360 (1995).
Lee et al., *Development* in press (1997).
Liem et al., . *Cell* 82, 969–979 (1995).
Marigo et al., *Dev. Biol.* 180, 273–283 (1996).
Marigo et al., *Proc. Natl. Acad. Sci. USA* 93, 9346–9351 (1996).
Martí et al.*Nature* 375, 322–325 (1995).
Mullor et al *Development* 124, 1227–1237 (1997).
Nohno et al., *Biophys Res Comm.* 206, 33–39 (1995).
Oro et al. (1997) *Science* 276:817–21.
Platt et al., *Mech. Dev.* in press (1997).
Roberts et al., *Cancer Research* 49, 5407–5413 (1989).
Roelink et al., *Cell* 76, 761–775 (1994).
Roessler et al., *Nature Gennetics* 14, 357–360 (1996).
Riddle et al.*Cell* 75, 1401–1418 (1993).
Ruppert et al.,*Molecular and Cellular Biology* 11, 1724–1728 (1991).
Ruppert et al., *Mol. Cell Biol.* 10, 5408–5415 (1990).
Ruiz i Altaba et al.,*Natl. Acad. Sci. USA* 90, 8268–8272 (1993).
Ruiz i Altaba et al., *Mech. Dev.* 44, 91–108 (1993).
Ruiz i Altaba et al., *Mol.Cell. Neurosci.* 6, 106–121 (1995).
Ruiz i Altaba, A. *In Essential Developmental Biology– A Practical Approach.* (C. Stern and P.W.H. Holland) IRL Press, Oxford (1993).
Salgaller et al., *Cancer Letters* 57, 243–253 (1991).
Scharen–Wiemers et al., *Histochemistry* 100, 431–440 (1993).
Shimizu et al., *J. Dermatol* 14, 359–363 (1987).
St–Jacques et al., 1998, Curr Biol, 8:1058–68.
Stone et al., *Nature* 384, 129–134 (1996).
Urano et al., *Society for Invest. Derm.* 104, 928–932 (1995).
van der Schroeff et al., *Society for Invest Derm* 94, 423–425 (1990).
von Ohnen et al., *Proc. Natl. Acad. Sci. USA.* 94, 2404–2409 (1997).
Wallace et al., *Arch. Pathol* 50, 199 (1950).
Walterhouse et al., *Developmental Dyn.* 196, 91–102 (1993).
Wilson et al., *Nature* 376, 331–333 (1995).
Xiao et al., . *Pediatr Neurosurg* 20, 178–182 (1994).

*Primary Examiner*—Phuong T. Bui
(74) *Attorney, Agent, or Firm*—Klauber & Jackson

(57) ABSTRACT

Methods for detection of the onset or presence of sporadic basal cell carcinoma in an animal by measuring for elevated levels of ectopic expression of Gli1 in the animal's epidermal tissue sample suspected of harboring sporadic basal cell carcinoma.

2 Claims, 7 Drawing Sheets

(5 of 7 Drawing Sheet(s) Filed in Color)

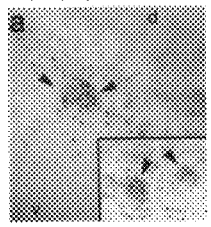
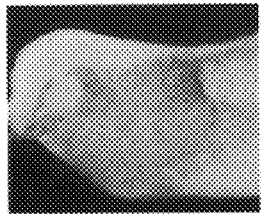
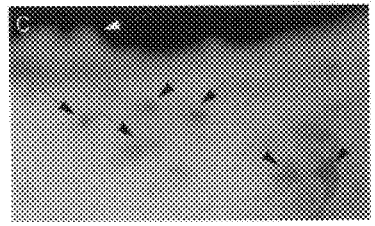
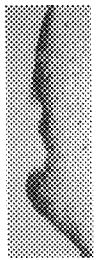
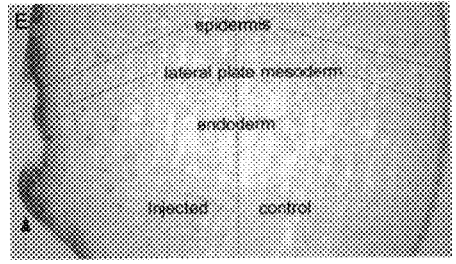
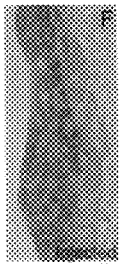
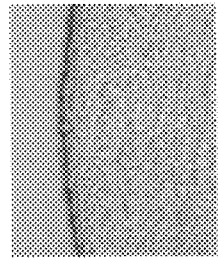
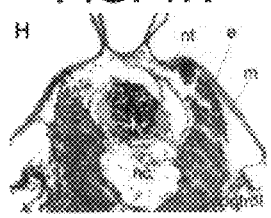
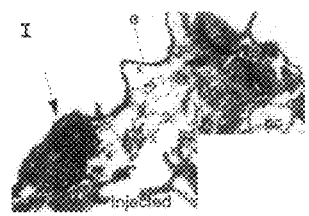

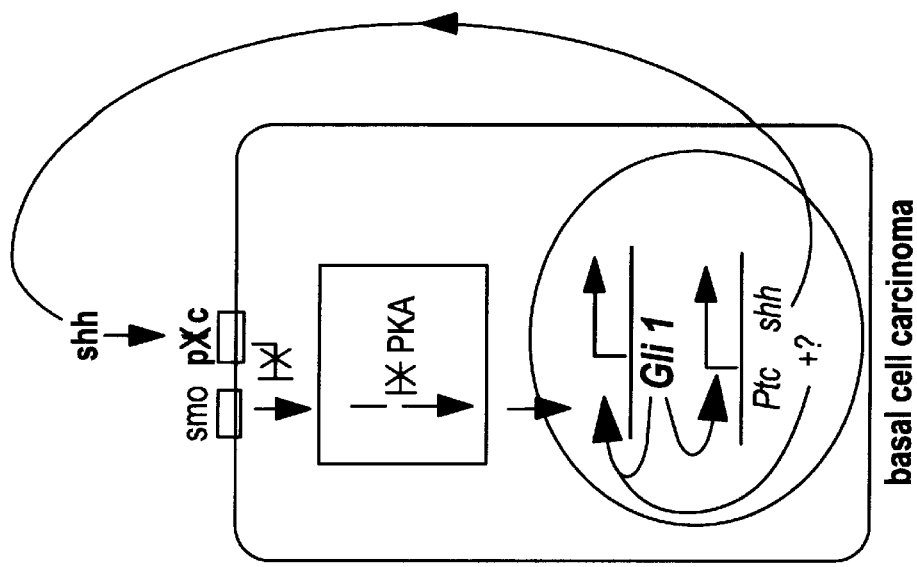
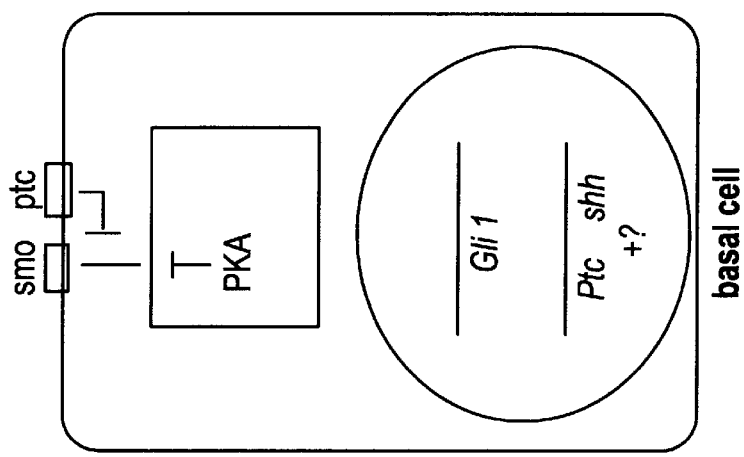
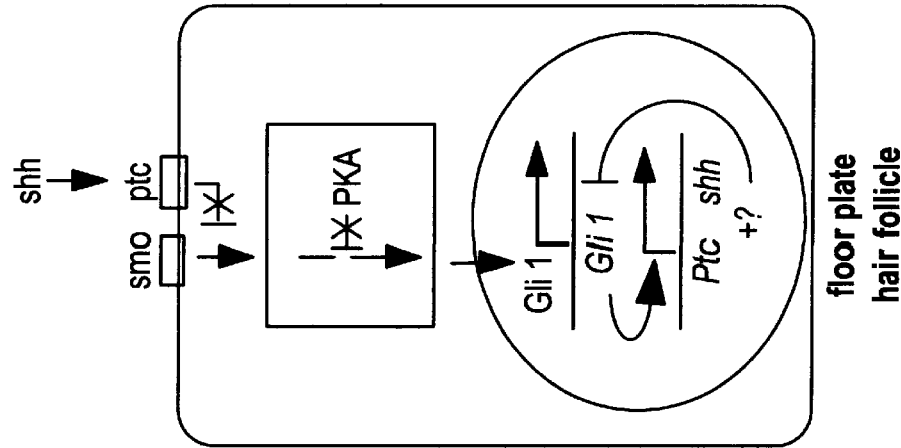

SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 1
cagagaatgg agcatcctcc                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
ttctggctct tcctgtagcc                    20

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 3
gcagccacag aatgtcc                       17

<210> SEQ ID NO 4
<211> LENGTH: 23

```
<212> TYPE: DNA
<213> ORGANISM: Artificial Sequence
<220> FEATURE:
<223> OTHER INFORMATION: Description of Artificial Sequence: Primer

<400> SEQUENCE: 4
agggatatcc aatcgaggaa tcg                                           23

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 5
gaagatctcc agaaactcc                                                19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
tcgtagtgca gagactcc                                                 18

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
gctatgtcac gcatctgatg                                               20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 8
cctcaatgat ctcctgatc                                                19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 9
agatgtctgc tgctagtcc                                                19
```

US 6,238,876 B1

METHODS AND MATERIALS FOR THE DIAGNOSIS AND TREATMENT OF SPORADIC BASAL CELL CARCINOMA

This application claims priority to provisional application number 60/050286, filed Jun. 20, 1997, now abandoned.

FIELD OF THE INVENTION

The present invention relates generally to the diagnosis and treatment of pathologies involving tumor formation and neoplasia, and more particularly to the detection of a condition of skin cancer known as sporadic basal cell carcinoma (BCC), and to the identification of relevant therapeutic agents based on their effect on the level of expression and/or activity of the gene Gli1, as well as to the preparation of therapeutic compositions and methods of use.

BACKGROUND OF THE INVENTION

Inductive signaling plays a critical role in both normal and disease development as developmental pathways that become unregulated in the adult can lead to abnormal patterning, overproliferation and neoplasia. One signaling pathway that is involved in several patterning events during embryogenesis is that triggered by secreted sonic hedgehog (Shh[1-4]). Shh binding to the membrane patched (ptc)-smoothened (smo) receptor complex elicits a cascade of cytoplasmic signal transduction events, including the inhibition of protein kinase A (PKA[5-12]) that leads to the transcription of the zinc finger transcription factor gene Gli1[11,13]. Gli1 is a proto-oncogene first isolated as an amplified gene in a glioma[14] that can transform fibroblasts in cooperation with E1A[15]. Gli1 is a member of a family comprising two other related genes: Gli2 and Gli3[16,17]. However, only Gli1 has been shown to be a target of Shh and mimic its effects[13]. In Drosophila, hedgehog signaling[18] similarly leads to the action of cubitus interruptus (ci), a Gli homolog that activates transcription of hedgehog-target genes[19-23].

One of the processes in which Shh signaling is involved is the differentiation of ventral neural tube cell types acting as a notochord and floor plate-derived signal[1,4,24-27]. Previous work by the applicants herein on the role of sonic hedgehog signaling during neural plate patterning in frog (*Xenopus laevis*) embryos demonstrated that cells becoming floor plate respond to Shh by expressing Gli1, Pintallavis and HNF-3β, critical transcription factors that themselves can induce the differentiation of floor plate cells[13,25,28,29].

In addition to effects on neural tissue, it has been found that ectopic expression of Shh and Gli1 also leads to the activation of Shh signaling target genes in epidermal non-neural ectoderm. Injected Shh induced the ectopic expression of Gli1, HNF-3β and Shh[25], and ectopic expression of Gli1 induced the ectopic expression of HNF-3β and Shh[13]. Together, these results indicated that both neural and epidermal cells have functional reception and transduction mechanisms for Shh and can respond by activating the expression of Shh/Gli1 target genes even though epidermal cells do not normally receive the Shh signal at this stage.

The citation of any reference herein should not be construed as an admission that such reference is available as "Prior Art" to the instant application.

SUMMARY OF THE INVENTION

In accordance with the present invention, methods and corresponding materials, including reagents and kits, are disclosed for use in the diagnosis of basal cell carcinoma (BCC), and particularly, sporadic BCC, which are based, at least in part, on the observation that there is a relationship between the ectopic expression of the gene Gli1 and the development onset or presence of BCC.

Accordingly, the invention in an initial aspect extends to a method for the diagnosis and detection of BCC in mammals, including humans, which comprises measuring the presence and level of ectopic expression of Gli1.

In a further aspect, the invention extends to an assay for the examination and diagnosis of the presence and extent of basal cell carcinoma in an animal, which comprises an observable test colony which exhibits a demonstrable development of tumor formation and/or neoplasia upon contact with ectopically expressed Gli1A–1Jfrom a biological sample taken from the animal.

Still further, the invention includes the development of therapeutic agents that are capable of controlling the expression and/or activity/function and expression of Gli1, and are thereby able to inhibit the development and/or treat sporadic basal cell carcinoma in animals, and particularly in humans. Such agents may include small molecules, ligands, and other agents that would function as Gli1 antagonists or would otherwise interrupt Gli1 expression and activity. Suitable pharmaceutical compositions could be administered by a variety of routes, including topical, oral, parenteral, intrathecal, intranasal, and the like, at a dosage level and schedule that may be determined by the clinician in accordance with the particular condition of the patient.

Accordingly, it is a principal object of the present invention to provide a method for the detection and diagnosis of basal cell carcinoma and particularly, sporadic basal cell carcinoma, that is efficient and accurate.

It is a further object of the present invention to provide a method as aforesaid that involves the observation and measurement of the level of expression of the gene Gli1 and/or its protein product.

It is a still further object of the present invention to provide assays for the performance of the methods as aforesaid that include an observable test colony capable of eliciting and exhibiting a demonstrable tumorigenic response upon stimulation with Gli1.

It is a still further object of the present invention to provide assays as aforesaid that may be used to screen for candidate inhibitors of basal cell carcinoma.

It is a yet further object of the present invention to provide therapeutic agents, compositions containing them, and corresponding methods of administration, that result from the identification and development of agents that act to modulate or control the activity or expression of Gli1 in animals, and particularly humans.

Other objects and advantages will become apparent to those skilled in the art from a consideration of the ensuing detailed description that proceeds with reference to the following illustrative drawings.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIGS. 1A–1J shows that the ectopic expression of Gli1 in frog embryos leads to the formation of epidermal tumors (1A through 1C) whole mount view of injected tadpoles (stages ~32–34) 51-4 showing the localization of epidermal mounds in the flank (1A, 1B) or posterior region (1C). The embryo shown in (1A) was injected with plasmid DNA driving the expression of the endogenous frog Gli1 cDNA and was then labeled with anti-HNF-3β antibodies. HNF-3β protein expression is detected in the epidermis including some cells in the tumor (see inset). The embryos shown in (1B, 1C) were co-injected with Gli synthetic RNA and LacZ RNA as tracer.

(1D through 1G) histological cross sections through the trunk of Gli1-injected embryos showing the cellular morphology of affected and control epidermal regions. (1D) Detail through the affected area of an embryo similar to that shown in (1A). Some cells within the tumor show expression of HNF-3β. (1E) Low magnification view of a cross section of an embryo similar to that shown in (1B) but also labeled with anti-HNF-3β. antibodies. The affected side is marked by the blue reaction product of x-gal staining (left). Note the absence of HNF-3β labeling in the epidermal tumor to the left but the presence of the normal pattern of expression in endodermal nuclei (b). The position of the lateral plate mesoderm and epidermis is marked. (1F) Detail of a tumor region from an embryo similar to that shown in (1C) where prominent b-gal activity is detected as small cytoplasmic inclusions. (1G) Detail of the normal flank epidermis of a control embryo shown as comparison to (1F). In (1F, 1G) the boundary between the epidermis and the underlying mesoderm in denoted.

(1H–1J) Histological sections stained with hematoxylin and eosin through the trunk of control (1H) and Gli1-injected (1I, 1J) stage ~45 tadpoles. An epidermal tumor is detected in the flank in (arrow, 1I). (1J) shows a higher magnification image of an outwardly growing epidermal tumor (arrow). e; epidermis, m; muscle, n: notochord, sc: spinal cord, t: tumor.

Arrows point to epidermal tumors. In all cases dorsal side is up. In (1A through 1C) anterior is to the left.

Figure 2A:
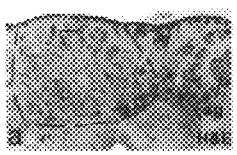
Figure 2B:
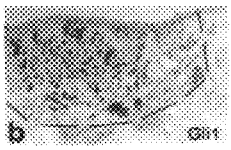
Figure 2C:
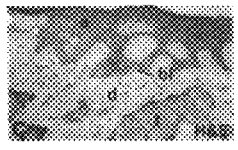
Figure 2D:
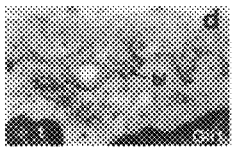
Figure 2E:
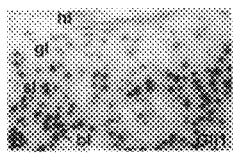
Figure 2F:
Figure 2G:
Figure 2H:
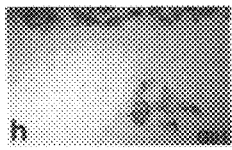
Figure 2I:
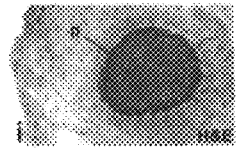
Figure 2J:
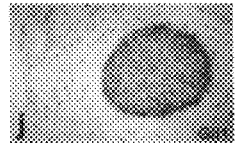
Figure 2K:
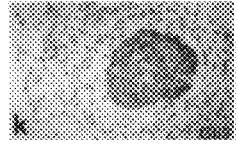
Figure 2L:
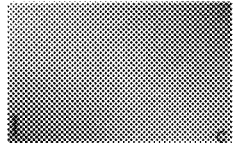
Figure 2M:
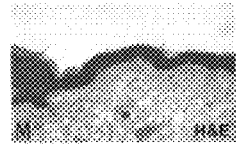
Figure 2N:
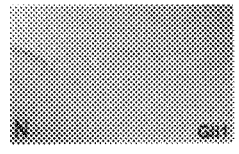
Figure 2O:
Figure 2P:
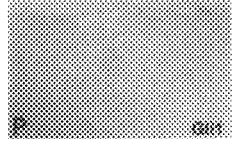

FIG. 2A–2P illustrates the expression of Gli1 and Gli3 in basal cell carcinomas (2A through 2L) Sections of BCC excisions showing the distribution of tumor masses as seen by hystological staining (2A, 2C, 2G, 2I), Gli1 mRNA expression as detected with antisense Gli1 RNA probes (2B, 2D, 2E, 2F, 2H, 2J) or Gli3 mRNA (2K). As control (c), absence of label is seen after hybridization with a Gli1 sense probe (2L). (2A) and (2B), (2C) and (2D), (2G) and (2H), and (2I through 2L) are matched samples from the same specimens, respectively. (2E) and (2F) show details of the specimen shown in (2A through 2D). Specific RNA expression is dark blue and was detected in the cytoplasms in most cases although others showed mostly nuclear signal.

(2M, 2N) Sections of normal skin regions distal from tumorigenic regions in a BCC excision showing the absence of Gli1 expression.

(2O, 2P) Sections of a biopsied sample of squamous cell carcinoma (SCC) showing the absence of Gli1 expression.

H&E: hematoxylin and eosin stain. bl: basal layer; d: dermis; e: epidermis; gl: granular layer; hl: horny layer; p: pallisade in the periphery of the tumor nodule; sl; spiny layer; t: tumor.

In all cases the skin surface is up except in (2I through 2L) where it is to the left.

Panels (2A–2F) show case # 5, panels (2G, 2H) show case # 7, panels (2I–2L) show case # 12, panels (2M, 2N) show a normal skin region of case #18, panels (2O, 2P) show case # 15, all as listed in Table 1.

FIG. 3A–3I illustrates the expression of Gli1 protein in basal cell carcinomas

Cells were labeled with anti-Gli1 antibodies (3A, 3C, 3E, 3G) or with the DNA-binding dye DAPI showing the position of nuclei (3B, 3D, 3F). (3A through 3D) show sections of excised BCC's with cytoplasmic Gli1 protein with highest levels in the periphery of tumor nodules (arrows). (3E, 3F) show Gli1 protein in Tera-1 human embryonal carcinoma cells localized predominantly to the nuclei although some protein is evident in the cytoplasm (arrow). Both (3D) and (3F) show double exposures where a hint of the distribution of Gli1 can be seen in relation to nuclei. (3G) Expression of Gli1 protein in COS-7 cells transfected with plasmids driving the expression of the human cDNA. Gli1 protein is predominantly nuclear although some cytoplasmic labeling is evident (arrows).

FIGS. 4A–4I demonstrates Shh expression in BCC's and induction of Shh expression by Gli1

(4A–4F) Expression of Gli1 and Shh in BCC's. (4A, 4D) show hematoxilin and eosin (H&E) stained panels identifying the presence of tumor infiltrating smooth muscle (m; 4A) or the dermis (4D). Sequential sections probes for Gli1 (4B, 4E) or Shh (4C, 4F) mRNA reveal the expression of these genes in tumor (t) cells. Arrows in (4D–4F) point to a similar position in all three panels. The lower levels of Shh expression are likely due to the short size of the RNA probed used. Panels (4A–4C) show case #26, panels (4D–4F) show case #30, as listed in Table 1.

(4G–4I) Frog tadpoles (stages 34–36) injected with Gli1 RNA (4G, 4I) showing exogenous expression of Gli1 (4G) or ectopic Shh (arrows, 4I) in the epidermis. Gli1 is normally expressed in several tissues including the neural tube but not in the epidermis[13]. A control embryo (4H) shows no expression of Shh in the epidermis (4H) with normal expression of this gene in the nervous system and head structures[25]. Anterior is to the left and dorsal side is up.

FIGS. 5A–5E demonstrates expression of Shh and Gli genes in mouse hair follicles (5A) Histological section of flank mouse skin showing the cellular morphology of hair follicles (hf) surrounded by the dermis (d) and the overlying epidermis (e) as seen after staining with hematoxylin and eosin (H&E). (5B–5E) expression of Shh (5B), Gli1 (5C), Gli2 (5D) and Gli3 (5E) in the bulb area of growing hair follicles (arrows). Gli3 is expressed in a wider area than Gli1 or Gli2 corresponding to cells located further away from the bulb region.

FIGS. 6A–6C shows that Shh signaling pathway and alterations leading to skin cancer.

Diagrams of the intercellular signaling of secreted Shh and the signal transduction patthway leading to the activation of target gene transcription. (6A) depicts the Shh signaling pathway in floor plate cells (see text for details and ref[13,18] for further references) and possibly in hair follicles. Shh binding to patched inactivates its repression of smoothen resulting in transmission of a signal through different cytoplasmic components including PKA, depited as a box. The exact position of PKA in the pathway is unresolved. The end result is the action of the zinc finger transcription factor Gli1. In frog embryos, Shh signaling leads to Gli1 transcription and the subsequent activation of Gli-target genes such as HNF-3β. Floor plate induction by Shh leads to the transcriptional activation of Shh itself in the newly induced floor plate. Because Gli1 transcription is not maintained neither in the mature floor plate[13] nor in keratinocytes distal from the hair bulb, a negative feedback mechanims is suggested.

(6B) Depicts the Shh signaling pathway thought to be silent in the embryonic epidermis and basal cells. Repression of the Shh signaling pathway may be achieved though the action of ptc and/or PKA (in red).

(6C) Activation of the Shh signaling pathway in BCC's. Putative effects of environmental damage leading to possible targets in the membrane, cytoplasm or nucleus that may lead to an activation of the pathway are denoted arrows (yellow). The positive actions of Gli1 and the absence of ptc are shown activating the pathway (green). Expression of Shh by BCC's could underly maintenance of BCC's (green). Other ways to activate the pathway (blue) may include rendering smo insensitive to repression by ptc, loss of PKA and independent upregulation of a putative activator (A) of Gli1, perhaps including Gli1 itself.

Figure 7:
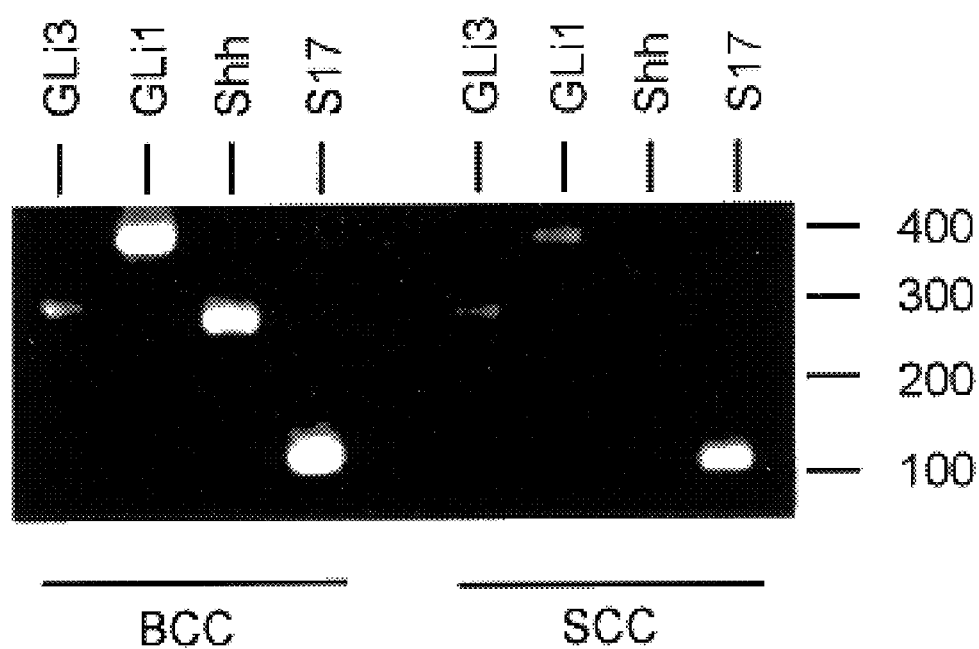

FIG. 7 shows Gli1, Gli3, Shh and S17 expression in BCC and SCC by RT-PCR.

DETAILED DESCRIPTION OF THE INVENTION

In accordance with the present invention there may be employed conventional molecular biology, microbiology, tissue/cell culture and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

In its broadest aspect, the present invention is predicated on the observation that there is a positive correlation between the ectopic expression of the gene Gli1 and the incidence and presence of basal cell carcinoma (BCC), and particularly, sporadic basal cell carcinoma in humans.

Accordingly, the invention includes a method for detecting the onset and presence of basal cell carcinoma in an animal, such as a human, by measuring the presence and expression of Gli1 in such animal. The methods may proceed by the examination of a biological sample taken from the subject under examination. The diagnostic methods can be used to detect Gli1 in a biological sample from an individual. Preferably, the biological sample is tissue, as Gli1 is generally detected in epidermal tissue, although some increased levels of Gli1 may be detectable in serum or urine, which are both readily obtained. Thus, the biological sample can also be a biological fluid, such as but not limited to, blood, serum, plasma, interstitial fluid, plural effusions, urine, cerebrospinal fluid, and the like. For example, cells can be obtained from an individual by biopsy and lysed, e.g., by freeze-thaw cycling, or treatment with a mild cytolytic detergent such as, but not limited to, TRITON X-100®, digitonin, NONIDET P (NP)-40®, saponin, and the like, or combinations thereof (see, e.g., International Patent Publication WO 92/08981, published May 29, 1992). In yet another embodiment, samples containing both cells and body fluids can be used (see ibid.).

Numerous possibilities both diagnostic and therapeutic are raised by the identification of the relationship between Gli1 expression and sporadic BCC. As suggested earlier and elaborated further on herein, the present invention contemplates pharmaceutical intervention in the cascade of reactions in which Gli1 appears to be implicated, to modulate its activity and to thereby control and possibly treat BCC in humans.

Thus, in instances where it is desired to reduce or inhibit the activity resulting Gli1 presence and expression, an appropriate inhibitor of such activity, or of Gli1 could be introduced to block the interaction of those factors causally connected therewith.

As discussed earlier, Gli1 or its binding partners or other ligands or agents exhibiting either mimicry or antagonism to it or control over its production, may be prepared in pharmaceutical compositions, with a suitable carrier and at a strength effective for administration by various means to a patient experiencing an adverse medical condition associated with Gli1 activity or expression specific for the treatment thereof. A variety of administrative techniques may be utilized, among them parenteral techniques such as subcutaneous, intravenous and intraperitoneal injections, catheterizations and the like. Average quantities of the therapeutic agent or the pharmaceutical composition may vary, and in particular should be based upon the recommendations and prescription of a qualified physician or veterinarian.

As suggested earlier, the diagnostic method of the present invention comprises examining a cellular sample or medium by means of an assay including an effective amount of an antagonist to a Gli1 protein, such as an anti-Gli1 antibody, preferably an affinity-purified polyclonal antibody, and more preferably a mAb. In addition, it is preferable for the anti-Gli1 antibody molecules used herein be in the form of Fab, Fab', F(ab')$_2$ or F(v) portions or whole antibody molecules. As previously discussed, patients capable of benefiting from this method include those suffering from cancer, a pre-cancerous lesion, a viral infection or other like pathological derangement. Methods for isolating the particular agent such as Gli1, and inducing anti-Gli1 antibodies and for determining and optimizing the ability of anti-Gli1 antibodies to assist in the examination of the target cells are all well-known in the art.

Methods for producing polyclonal anti-polypeptide antibodies are well-known in the art. See U.S. Pat. No. 4,493, 795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a Gli1-binding portion thereof, or Gli1. or an origin-specific DNA-binding portion thereof.

The present invention may be better understood by reference to the following non-limiting Examples, which are provided as exemplary of the invention.

METHODS

Embryos and Microinjection

*Xenopus laevis* embryos were obtained by standard procedures[63]. Microinjections were performed into the animal-most region of one cell at the two-cell stage in order to bias the distribution of the injected plasmids or RNAs to the ectoderm and to have one half of the embryo as undisturbed internal control[63]. 2 ng of synthetic RNAs made by in vitro transcription or 200 pg of plasmid DNA were delivered by microinjection. Frog Gli1, human Gli1 and Gli3 plasmids were as described[13].

In Situ Hybridization, Immunocytochemistry, Histology and Cell Lines

Frog embryos were processed for in situ hybridization with digoxygenin-labeled RNA probes following the Harland protocol with minor modifications [13]. Frog Gli1 and Shh plasmids to make sense or antisense RNA probes were as described[13]. In situ hybridization of frozen cryostat sections of tumor specimens excised by the Mohs technique were processed by in situ hybridization with digoxygenin-labeled RNA probes[64] Plasmids with human Gli1 and Gli3 cDNAs[14,16] and mouse Shh and Gli1-3 cDNAS used to make sense and anti-sense RNA probes were as described[13]. The human Shh probes were made from a plasmid subclone of a 409 bp RT-PCR product.

Immunocytochemistry with anti-human Gli1 affinity-purified polyclonal antibodies[13], anti-frog HNF-3β or anti-rat HNF-3β polyclonal antibodies[25] were performed by standard techniques by whole mount labeling or in 5–15 μm cryostat sections. Nuclei were visualized by staining with the DNA-binding dye DAPI after antibody incubations.

Histological sections of injected tadpoles were obtained by cutting paraplast-embedded samples in a microtome[13]. These sections and one section of each tumor sample were also stained with hematoxylin and eosin by standard techniques for histological examination. β-galactosidase activity was revealed by the X-gal reaction using standard techniques.

COS-7 and Tera-1 cells were obtained from ATCC and cultured under the specified conditions. Transfectiosn were performed with lipofectamine (GIBCO-BRL) as specified by the manufacturer. Cells were assayed 24–48h after transfection.

RNA Isolation and RT-PCR

RNA from frozen excisions was extracted by the guanidinium isothiocyanate, acid phenol method. Samples were immediately dissolved in guanidinium. cDNA was made with random hexamers and BRL Superscript reverse transcriptase. PCR was performed at 57° C. for 40 cycles with the following primers to human Gli1, Gli1-U: CAGAGAATGGAGCATCCTCC (SEQ ID NO: 1) and Gli1-D: TTCTGGCTCTTCCTGTAGCC (SEQ ID NO: 2) yielding 412 bp product; to human Gli3, Gli3-U: GCAGC-CACAGAATGTCC (SEQ ID NO: 3) and Gli3-D: AGG-GATATCCAATCGAGGAATCG (SEQ ID NO: 4) yielding a 293 bp product; to human Shh, Shh-U2: GAAGATCTC-CAGAAACTCC (SEQ ID NO: 5) and Shh-D: TCGTAGT-GCAGAGACTCC (SEQ ID NO: 6) yileding a 233 bp product; and to mouse S17 which works well with human cDNA, S17-U: GCTATGTCACGCATCTGATG (SEQ ID NO: 7) and S17-D: CCTCAATGATCTCCTGATC (SEQ ID NO: 8) yielding a 137 bp product. The RT-PCR Shh clone used to make RNA probes derived from a reaction using Shh-U1:

AGATGTCTGCTGCTAGTCC (SEQ ID NO: 9) and Shh-D.

EXAMPLE 1

In this experiment, the effects of deregulated Gli1 expression and the activation of the Shh signaling pathway in the epidermis were investigated, using the frog embryo as a model system. We show that ectopic Gli1 expression in the epidermal ectoderm of frog embryos results in tumor formation, that Gli1 and Shh are normally expressed in the hair follicles of the adult mammalian epidermis and that human sporadic basal cell carcinomas (BCC's) consistently express Gli1. We have previously shown that Gli1 acts as a target and mediator of Shh signaling[13]. Thus, our results suggest that activation of Shh signaling leading to Gli1 expression in the epidermis will cause BCC formation. This is consistent with the loss of function of the Shh receptor ptc, which acts negatively on the pathway, in familial and a fraction of sporadic BCC's[30-32].

Ectopic Expression of Gli1 Induces Tumor Formation in the Tadpole Epidermis

Frog embryos injected with plasmids driving the expression of the endogenous frog Gli1 gene displayed ectopic expression of HNF-3β in the skin (85%, n=25[13]). As expected, injected embryos also expressed this gene in the neural tube (not shown[13]). In addition, these embryos developed abnormal mounds in the otherwise normal smooth epidermis of the tadpole (78%, n=25; FIG. 1a). Similar results were obtained with the human Gli1 cDNA (70%, n=10; not shown). Because the plasmid DNA was targeted to the animal most region of the 2-cell embryo, only ectodermal derivatives inherit plasmids[25] indicating that the mounds of focal epidermal hyperplasia or tumors observed are caused by expression of Gli1 in the epidermis and not in the underlying lateral plate mesodem. Indeed, detection of epitope-tagged Gil1 in injected embryos showed exclusive expression in the ectoderm (not shown[13]). A number of these epidermal tumors contained cells which expressed HNF-3β (30%, n=27; FIG. 1a, d).

Embryos injected with plasmids driving the expression of endogenous frog Gli1 were grown for 1 week (stage ~45) in order to assess the morphological development of induced epidermal tumors. Histological sections of injected tadpoles revealed tumors in the epidermis (FIG. 1i, j), sometimes consisting of densely packed cells (FIG. 1i), not found in normal controls (FIG. 1h). These cells were clearly distinct from all normal tissues. Together, these results show that transient epidermal expression of Gli1 leads to tumor formation in vivo.

EXAMPLE 2

Cells Expressing Gli1 Become Tumorigenic

To determine if tumors formed from cells inheriting the injected Gli1 RNA, lineage tracing analysis was performed by injection of synthetic RNA. Frog embryos were coinjected with Gli1 mRNA and a small amount of LacZ mRNA as tracer. Injected embryos displayed β-galactosidase (β-gal) activity in the epidermis and neural ectoderm of the injected half. Injection of LacZ mRNA alone caused no detectable defects in the injected embryos and all embryos injected with Gli1 mRNA displayed ectopic HNF-3β expression within the neural tube (not shown).

The epidermis of injected embryos displayed atypical morphology. Externally, injected tadpoles showed prominent tumors of the skin (80%; n=12) that were always associated with β-gal activity (FIG. 1b, c). Histological analysis of these embryos revealed that the tumors formed from the superposition of epidermal cells that inherited Gli1 mRNA, as these cells invariably expressed β-gal (FIG. 1e, f). Labeled epidermal cells located inside the tumors were distinct from the underlying lateral plate mesoderm which was always unlabeled. In contrast to the injected side, the uninjected side displayed typical smooth embryonic epidermis (FIG. 1e, g). Expression of HNF-3β in these Gli1-induced tumors was infrequent (10%, n=12) indicating that its expression and epidermal tumor formation are independent events. Because not all epidermal cells inheriting Gli1 RNA become tumorigenic there could be a requirement for a certain level of Gli1 to initiate tumor formation. The effects of Gli1 are specific as injection of plasmids driving the expression of the related gene Gli3[16] or synthetic Gli3 RNA had no effect (n=45; not shown[13]).

These experiments demonstrate that inappropriate expression of Gli1 leads to tumor formation although it is not clear if this represents epidermal neoplastic transformation in the early tadpole.

Gli1 is Selectively Expressed in Sporadic Human BCC's

The epidermal ectoderm of early vertebrate embryos becomes the basal layer of the adult epidermis and these two cell types have common properties. For example, mouse basal-specific keratins are also expressed in the early embryonic monolayered epidermis[33]. Basal cells play a critical role in skin development as these are progenitors that produce daughter cells that replenish the keratinized outer layers. The mechanisms of basal epidermal cell maintenance and embryonic epidermal development in vertebrates could therefore be similar, raising the possibility that the defects observed in the epidermis of Gli1-injected embryos may resemble defects of abnormal basal cell development in the adult.

In this context, the recent demonstration that mutations in the patched (ptc) gene underlie the human familial basal cell nevus syndrome[30,31] is intriguing. Ptc is a component of the receptor complex for Shh having a constitutive negative effect that is repressed by Shh bindings[12,18,34,35]. Thus, mutation of the ptc receptor may lead to constitutive Shh signaling in the absence of the ligand. This, in fact, would appear to be similar to the activation of the Shh signaling pathway either through the ectopic expression of the ligand, Shh, or the activation of a downstream target and mediator: Gli1[13] (FIG. 6a). Together, the finding of mutated ptc alleles in familial and some sporadic BCC's[30-32], and the development of skin tumors in tadpoles expressing Gli1 ectopically raised the possibility that ectopic Gli1 expression could be expressed in and underlie the development of sporadic adult basal cell cancer through the activation of the Shh signaling pathway.

EXAMPLE 3

To address the possibility that Gli1 activation and ectopic expression could play a role in the development of adult sporadic BCC, spontaneously occurring human BCC's were assayed for Gli1 expression. Sections of fresh excised specimens were analyzed by in situ hybridization with digoxygenin-labeled antisense RNA probes. All but one of the samples examined showed unambiguous expression of Gli1 mRNA although the level of expression varied ($^{17}/_{18}$; Table 1; FIG. 2). The variability observed in Gli1 RNA expression could be due to inherent differences of the tumors or to differences in the preservation of the material after excision. No correlation was detected between the level of Gli1 expression and the site or the aggressiveness of the tumor. In contrast to the prevalent expression of Gli1, only one half ($^{6}/_{12}$; Table 1) of the cases displayed unequivocal expression of the related gene Gli3 (FIG. 2k) which is often coexpressed with Gli1 [11,13,17,36]. Analysis of three cases of squamous cell carcinoma (SCC) in situ showed the absence of Gli gene expression (Table 1; FIG. 2o, p). Control hybridizations with sense RNA probes showed no signal (Table 1; FIG. 2l).

TABLE 1

Gene expression in human skin tumors a
In situ hybridization and immunocytochemistry

| Case | type | location | GU1 Ab | HNF-3β Ab | GH1-as | GH1-a | GH3-as | GH3-a | Shh-as | Shh-a | Ptc-as | H&E |
|---|---|---|---|---|---|---|---|---|---|---|---|---|
| 1 | BCC | auricular | + | | | | | | | | | + |
| 2 | BCC | nasolabrial fold | + | − | | | | | | | | + |
| 3 | BCC | temple | + | − | | | | | | | | + |
| 4 | BCC | forehead | + | | | | | | | | | + |
| 5 | BCC | post-auricular | | | ++ | | | | | | | + |
| 6 | BCC | inner canthus | + | − | ++ | | | | | | | + |
| 7 | BCC | post-auricular | + | − | ++ | − | | | | | | + |
| 8 | BCC | nosolabial fold | | | ++ | | | | | | | + |
| 9 | BCC | post-auricular | | | ++ | | | | | | | + |
| 10 | BCC | canthus | | | +/− | − | +/− | | | | | + |
| 11 | BCC | canthus | | | + | − | + | | | | | + |
| 12 | BCC | back | | | ++ | − | ++ | − | | | | + |
| 13 | BCC | nasal rim | | | ++ | − | − | | | | | + |
| 14 | BCC | nr | | | ++ | − | − | − | | | | + |
| 17 | BCC | nr | | | +/− | − | − | − | | | | + |
| 18 | BCC | nr | | | ++ | − | − | − | | | | + |
| 24 | BCC | nose | | | + | | − | | + | | | + |
| 26 | BCC | periareolar | | | ++ | | + | | ++ | − | | + |
| 27 | BCC | eyelid | | | + | | − | | − | − | | + |
| 28 | BCC | nose | | | + | | +/− | − | − | | | + |
| 29 | BCC | temple | | | + | | + | | + | − | | + |
| 30 | BCC | midback | | | ++ | | + | | + | − | | + |
| 32 | BCC | lat. forehead | | | + | | − | | − | | | + |
| 33 | BCC | eyebrow | | | + | | + | | + | | | + |
| 34 | BCC | noseop | | | + | | + | | − | | | + |
| 37 | BCC | lat. upper cheek | | | +/− | | +/− | | +/− | | | + |
| 39 | BCC | upper lip | | | + | | + | | +/− | | | + |
| 41 | BCC | molar ocular | | | ++ | | ++ | | +/− | | | + |
| 42 | BCC | molar ocular | | | ++ | | + | | − | | | + |
| 43 | BCC | temple | | | ++ | | + | | − | | | + |
| 44 | BCC | nose | | | + | | + | | − | | | + |
| 45 | BCC | cheek | | | ++ | | + | | + | | | + |
| 46 | BCC | nostril | | | ++ | | ++ | | − | | | + |
| 47 | BCC | rygoma | | | ++ | | + | | − | | | + |
| 48 | BCC | upper eyelid | | | + | | ++ | | + | | | + |
| 51 | BCC | glabella | | | ++ | | + | | + | | | + |
| 52 | BCC | nose | | | + | | ++ | | − | | | + |
| 53 | BCC | nose | | | + | | +/− | | − | | | + |
| 54 | BCC | ear | | | ++ | | +/− | | +/− | | | + |
| 57 | BCC | clavicle | | | + | | − | | − | | | + |
| 59 | BCC | nose | | | ++ | | | | + | − | ++ | + |
| 61 | BCC | nose | | | ++ | | | | ++ | − | + | + |
| 63 | BCC | nose | | | + | | | | | | ++ | + |
| 64 | BCC | forehead | | | +/− | | | | − | − | ++ | + |
| 66 | BCC | temple | | | + | | | | − | − | + | + |
| 67 | BCC | forehead | | | + | | | | + | − | ++ | + |
| 69 | BCC | forehead | | | ++ | | | | − | − | ++ | + |
| 70 | BCC | scalp | | | ++ | | | | − | − | ++ | + |
| 71 | BCC | eye | | | + | | | | − | − | + | + |
| 72 | BCC | nose | | | ++ | | | | − | − | ++ | + |
| 74 | BCC | temple | | | + | | | | − | − | + | + |
| 15 | SCC | upper back | | | − | − | − | − | | | | + |
| 23 | SCC | preauricular | | | − | | − | | − | − | | + |
| 25 | SCC | eyelid | | | − | | − | | − | − | | + |
| 31 | SCC | elbow | | | − | | − | | − | − | | + |
| 35 | SCC | cheek | | | − | | − | | − | | | + |
| 40 | SCC | cheek | | | − | | − | | − | | | + |
| 49 | SCC | cheek | | | − | | − | | − | − | | + |
| 55 | SCC | hand | | | − | | +/− | | − | | | + |
| 56 | SCC | neck | | | − | | − | | − | | | + |
| 58 | SCC | bridge nose | | | − | | − | | − | | | + | b

TABLE 1-continued

Gene expression in human skin tumors

| | | | RT-PCR of whole exciseism | | | | |
|---|---|---|---|---|---|---|---|
| Case | type | location | GH1 | GH3 | Shh | Fic | S17 |
| 19 | BCC | nose | ++ | + | + | ++ | + |
| 20 | BCC | rear | ++ | + | + | ++ | + |
| 22 | BCC | infracbital | ++ | + | − | ++ | + |
| 52 | BCC | nose | ++ | + | − | ++ | + |
| 53 | BCC | nose | ++ | + | − | ++ | + |
| 21 | SCC | finger | + | + | − | + | + |
| | | fetal brain | ++ | ++ | ++ | + | + |

Tumor nodules infiltrating the dermis showed the highest levels of Gli1 expression (FIG. 2a–f, i, j) and here it was concentrated in the periphery (FIG. 2f, j), where the majority of proliferating cells are located[37]. In tumorigenic regions, the basal layer of the epidermis also displayed high levels of Gli1 expression as compared to more superficial layers where decreasing levels of Gli1 gene expression were detected (FIG. 2c–e). The pattern of expression of Gli3 was distinct from that of Gli1 but was also primarily detected in the periphery of tumor nodules (FIG. 2k). Gli gene expression was detected neither in the epidermis nor in the dermis in normal regions distal from the tumor (FIG. 2m, n), although Gli1 mRNA was detected in histologically normal basal cells immediately surrounding the tumor site (right side in FIG. 2a, b). Cells of the sebaceous glands, dermis and blood vessels were negative. Single cells surrounding major BCC tumor masses were sometimes positive for Gli1 (3/18) or Gli3 expression (1/12; FIG. 2j, k). These cells could represent early invading tumor cells that are histologically unrecognizable. Alternatively, these single cells may be non-BCC cells which express Gli1 expression in response to a secreted tumor-derived factor.

EXAMPLE 4

Gli1 Protein is Primarily Cytoplasmic in BCC's

Figure 3A:
Figure 3B:
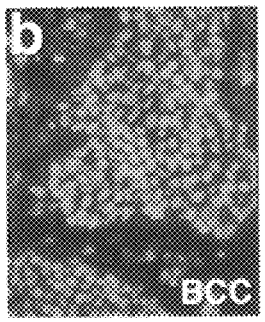
Figure 3C:
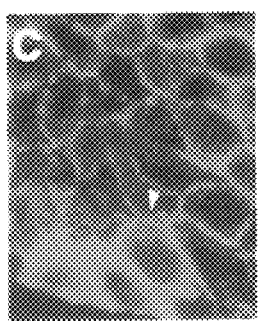
Figure 3D:
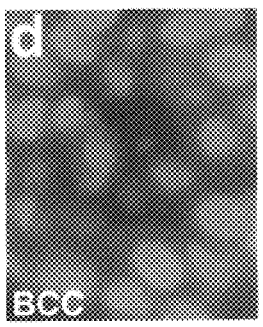

Expression of Gli1 was also analyzed by immunocytochemistry with an affinity purified anti-human Gli1 polyclonal antibody that does not recognize Gli3[13]. All samples showed specific Gli1 expression (5/5; Table 1; FIG. 3a–d). Control antibody labeling with an anti-HNF-3β polyclonal antibody[25] showed no specific labeling (Table 1 and not shown). As with the mRNA, Gli1 protein levels were highest in the periphery of tumor nodules (FIG. 3a, c).

Figure 3E:
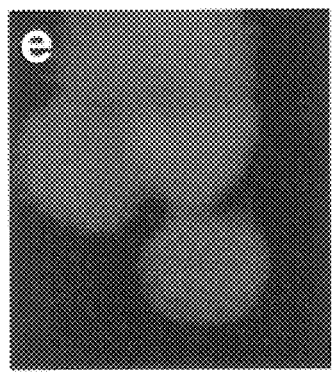
Figure 3F:
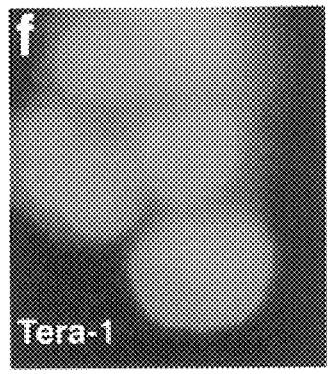
Figure 3G:
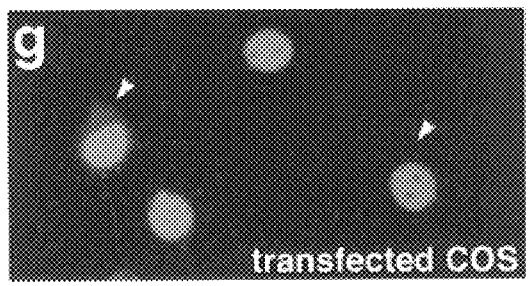

In BCC's, Gli1 protein was detected in the cytoplasm with higher levels in apparent association with the membrane (FIG. 3a, c). This contrasts with the nuclear localization of Gli1 protein in i) COS cells transfected with the glioma-derived cDNA[13] (FIG. 3g), ii) a glioma line with a 75-fold overexpression of Gli1 (D259MG[14,38]), and iii) human embryonal carcinoma Tera-1 cells that show a ten-fold overexpression of Gli1[38] (FIG. 3e, f). However, Tera-1 cells and transfected COS cells also display lower levels of labeling in the cytoplasm (FIG. 3e–g), and Drosophila ci, is normally localized mostly in the cytoplasm[39]. Moreover, frog Gli1 protein also appears to be mostly cytoplasmic[13].

Expression of Shh in BCC's

Our results with Gli1 and the inactivation of ptc in patients with the basal cell nevus syndrome[30,31] raised the possibility that components of the Shh signal transduction pathway, including endogenous human Shh itself[40,41], could be expressed in sporadic BCC's. This possibility is suggested by the regulatory loop defined in the Shh signaling pathway (FIG.6; see also ref.[18] for the Drosophila hh pathway) in which secreted Shh binds to the ptc/smo receptor complex triggering a cascade of events that leads to the activation of Gli1. Gli1 then acts to activate the transcription of Shh target genes including Shh and ptc.

Two cases of BCC showed Shh expression by RT-PCR whereas this was below the level of detection in one case of BCC and one of SCC in situ (Table Ib; FIG. 7). All samples showed low levels of Gli3 expression and all three BCC's , but not the SCC, showed elevated levels of Gli1 RNA. By in situ hybridization, 4/6 BCC's were positive for Shh with expression localized to the tumor masses that also expressed Gli1 (FIG. 4a–f; Table 1). Analysis of three cases of SCC's in situ showed no Shh expression (Table 1). Sense Shh RNA probes showed no specific signal (Table 1). The lower frequency of Shh (% cases overall) versus Gli1 expression (20/21 cases overall) in BCC's together with the inability of injected Shh to initiate epidermal tumor formation in frog embryos[25,42,43] suggest that Shh is unlikely to be the initial cause of Gli1 expression in BCC's.

Induction of Shh by Gli1

Gli1 may direct expression of Shh in BCC's. Frog embryo microinjection results in the widespread distribution of the injected Gli1 RNA in the epidermis.

Figure 4A:
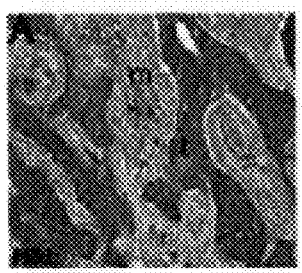
Figure 4B:
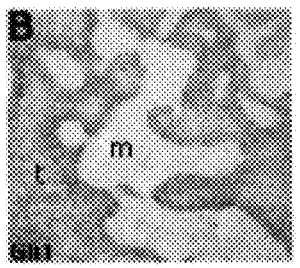
Figure 4C:
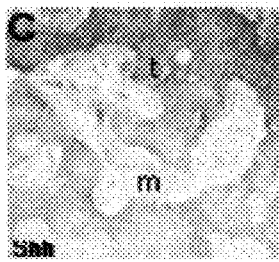
Figure 4D:
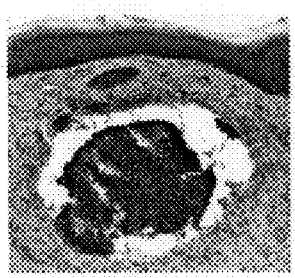
Figure 4E:
Figure 4F:
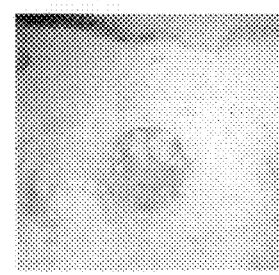
Figure 4G:
Figure 4H:
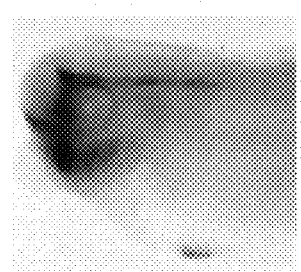
Figure 4I:
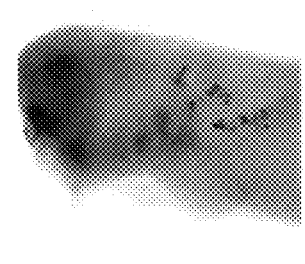
Figure 5A:
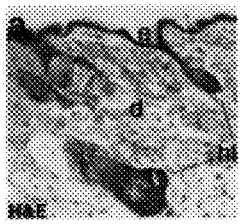
Figure 5B:
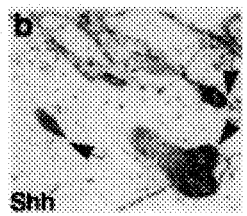
Figure 5C:
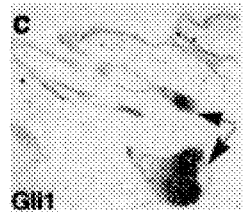
Figure 5D:
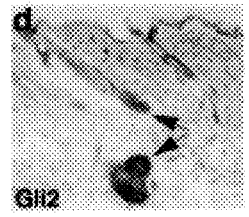
Figure 5E:
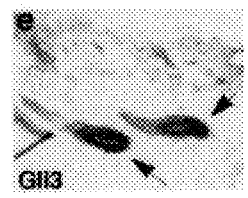

However, very high levels of Gli1 were observed at sites of tumor formation (60%; n=24; FIG. 4g) suggesting autoregulation by Gli1. A fraction of these embryos showed ectopic Shh in the epidermis of the tadpole (12%, n=25; FIG. 4i) and of early neurulae[13], not observed in controls (FIG. 4h). Similarly, injected Gli1 induces ectopic Shh expression in the neural ectoderm[13].

In addition to Shh, the transcription of ptc could also be downstream of Gli1 function in BCC's (FIG. 6) as ectopic induction of ptc can be driven by Shh in early embryos[7,9] and overexpression of ptc has been detected in sporadic BCC's analyzed[32]. Thus, it appears that in epidermal ectoderm, Shh can induce Gli1 expression and Gli1 in turn induces the expression of ptc and Shh, closing a regulatory loop. This is further suggested by the autoregulation of ectopic Shh in the epidermis[25].

Shh and Gli Gene Expression in Developing Follicles

Basal cells and the embryonic epidermis normally do not express Gli genes[13] (FIG. 5) and the reason why the epidermis is responsive to Shh and Gli1 is not clear. However, in excised specimens, very weak expression of Gli1 was detected in hair follicles (not shown). To further test expression of Gli1 in follicles, we analyzed the normal expression of Shh, Gli1, Gli2 and Gli3 in normal mouse skin. Specific labeling was detected in hair follicles during the growing phases with highest expression in matrix keratinocytes of the bulb (FIG. 5). As in follicles, coexpression of the three Gli genes has been observed in other embryonic tissues[13,17,36,44]. Expression of Shh in hair follicles[45,46] (FIG. 5) is consistent with it expression in feather buds[47]. In addition to Gli1 and Shh, it is likely that other members of the Shh signaling pathway, including ptc, are also expressed in the growing follicles.

These expression patterns indicate that normal epidermal development involves the selective activation of Shh and Gli genes, and thus the Shh signaling pathway, during follicular formation. Because follicles undergo succesive rounds of growth in which basal-like epidermal cells divide to give rise to the bulb of the growing hair, the expression of Gli1 and Shh in these epidermal structures provides a context for the ability of embryonic and non-follicular basal epidermal cells to respond to ectopic Gli1.

Gli1 and BCC Formation

Our experimental results in frog embryos in which ectopic Gli1 expression leads to epidermal tumor formation together with the striking correlation of Gli1 expression and BCC's strongly suggest a causative role of Gli1 in basal cell cancer. At present, it is unclear if ectopic Gli1 expression in tissues other than the epidermis will result in tumor formation. The high incidence of Gli1 expression in BCC's contrasts with the relative infrequent occurrence of other oncogenes such as mutated ras alleles[48]. However, expression of bcl-2 has been consistently detected in BCC's suggesting that bcl-2 could also be involved in BCC formation although it is normally expressed in basal cells[49]. Gli1 expression is not correlated with other cancers as it was found to be amplified only in a small number of gliomas and other tumors[14,50-53]. It is unclear if the varying expression levels of Gli1 in BCC's is due to differential amplification. It appears, therefore, that normal basal epidermal development and maintenance requires the constitutive repression of Shh signaling (FIG. 6b) and that inappropriate Gli1 transcription leads to BCC development. It is important to note that because there may be a regulatory loop in the Shh signaling pathway in BCC's (FIG. 6c) Gli1 expression would be predicted to be both a cause and an effect of BCC development.

Activation of Shh Signaling Leading to Gli1 Expression: A Molecular Pathway for BCC Formation It is not known at present what initiates or drives the ectopic expression of Gli1 in the epidermis at sites of sporadic BCC formation. We propose that any mutations that activate the Shh signaling pathway will lead to ectopic Gli1 transcription and thus, based on our frog experiments, to BCC formation. In familial BCC's showing loss of ptc function, we predict that Gli1 will be ectopically expressed as absence of ptc, a negative regulator of Shh signaling, would activate the pathway and thus Gli1 expression (FIG. 6c). However, mutations in ptc cannot account entirely for Gli1 activation. We found $20/21$ cases of sporadic BCC's expressing Gli1 whereas in one study only $1/12$ of the analyzed sporadic BCC's showed an altered ptc allele[31] and in another study mutations in ptc were detected in one third of the sporadic BCCs analyzed[32]. Moreover, $3/5$ BCC's analyzed showed ectopic expression of ptc but mutations in this gene were found in one case only[32]. Other potential causes for BCC induction in the Shh pathway include inactivation of PKA, ectopic expression of the factors initiating and maintaining Gli1 expression, possibly Gli1 itself, and perhaps ectopic Shh expression (FIG. 6c).

The inability of Shh to induce tumor formation in the tadpole epidermis and its inconsistent expression in BCC's raises the possibility that there may be restrictions to the induction and action of Shh in epidermis similar to those present in the neural plate[25]. The molecular basis of such restrictions is not known but could prevent BCC formation adjacent to follicle cells expressing Shh during normal hair growth and possibly after plucking. Moreover, these restrictions could prevent the uncontrolled spread of BCC's throughout the surrounding basal cells after induction of Shh expression. Independent of whether Shh can initiate BCC formation, its expression in BCC's suggests a mode of autocrine tumor maintenance as secreted Shh from the tumor cells could activate its signaling pathway leading to new expression of Gli1 (FIG. 6c). Activation of autocrine Shh signaling or autoregulation of Gli1 could underly the formation of persistent epidermal tumors in embryos that transiently expressed Gli1 through microinjection.

Do BCC's Arise From Inappropriate Follicular Development in Basal Cells?

Since hair follicles normally activate the Shh signaling pathway during growth, BCC's could derive from the neoplastic transformation of these cells. Indeed, follicular stem cells have been suggested to be targets of skin carcinogens[54]. In this case, BCC's would abnormally maintain active Shh signaling. However, Gli1 causes tumor formation in the tadpole epidermis which lacks both follicles and normal expression of Gli1. It is possible, therefore, that a variety of genetic and environmental signals converge to activate inappropriate Shh signaling at different levels leading to ectopic Gli1 transcription in non-follicular basal cells. In addition, in BCC's that may not harbor direct activating mutations within the Shh signaling pathway, the normal interaction taking place between the dermal papilla and the hair bulb could be inappropriately activated in non-follicular basal cells resulting in the activation of the Shh signaling pathway and BCC formation.

Targets of environmental damage could also include components of BMP signaling pathways having an indirect positive effect on Shh signaling. BMP4 and BMP2 are expressed in the mesenchyme that give rise to the dermal papilla and precortical region of the hair bulb, respectively, and ectopic BMP4 suppresses proliferation of hair follicles[55]. This is consistent with the mutual antagonistic effects of BMP's and Shh in the neural tube[56] and the requirement of BMP4 signaling[57] and repression of Shh signaling for normal embryonic epidermal development.

The parallel between activation of Shh signaling in the hair bulb and BCC's is consistent with the finding that BCC's show traits of follicular differentiation[58-60]. For example, an anti-keratin antibody selectively labels both BCC's and the follicular epithelium[61]. In addition to Gli1, the expression of Gli3 and Gli2 could represent distinct levels in follicularization as these genes are normally coexpressed with Gli1 in the growing hair bulb. The lack of expression of Shh and Gli genes in SCC's point to their very different nature[59,60]. Testing for the expression of these genes in benign "follicular" neoplasms, such as trichoepitheliomas, may clarify the identity of these tumors and provide a molecular correlate to malignancy.

Gli1 Expression as a Diagnostic Tool

BCC's are the most frequent malignant tumor in adult fair-skinned people. Although they rarely metastisize, sporadic BCC's represent a major health and economic problem[59]. The recurrence of BCC's at sites adjacent to previous tumors could result from the observed ectopic expression of Gli1 in basal cells in a wide region extending beyond the neoplastic sites, similar to the expansion of mutant p53 clones in BCC's to adjacent cells[62]. This raises the possibility that Gli1 expression in basal cells is an early event and could be used as a diagnostic tool. Finally, therapeutic agents for BCC's are likely to include inhibitors of the Shh signaling pathway.

The molecular basis of skin carcinogeneis is not known. We find that ectopic expression of the zinc finger transcription factor Gli1 in the ectoderm of frog embryos leads to the development of epidermal tumors. In addition, we find that sporadic basal cell carcinomas in adult humans display consistent expression of Gli1 and that in the normal skin Gli1 and Shh are expressed in developing follicles. Because Gli1 is involved in the interpretation of Shh signal, repression of Shh signaling is thus required for normal embryonic epidermal development and adult basal cell maintenance. Moreover, our results strongly suggest that Gli1 plays a causative role in this common human cancer, in which cells may be attempting follicular development. We predict that any mutations activating the Shh signaling pathway leading to Gli1 expression in the epidermis will cause basal cell cancer.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties. A list of references is provided below.

1. Echelard, Y., Epstein, D. J., St-Jacques, B., Shen, L., Mohler, J., McMahon, J. A. & McMahon, A. P. Sonic hedgehog, a member of a family of putative signaling molecules, is implicated in the regulation of CNS polarity. *Cell* 75, 1417–1430 (1993).
2. Riddle, R., Johnson, R. L., Laufer, E. & Tabin, C. Sonic hedgehog mediates the polarizing activity of the ZPA. *Cell* 75, 1401–1418 (1993).
3. Krauss, S., Concordet, J.-P. & Ingham, P. W. A functionally conserved homolog of the Drosophila segment polarity gene hedgehog is expressed in tissues with polarizing activity in zebrafish embryos. *Cell* 75, 1431–1444 (1993).
4. Roelink, H., Augsburger, A., Heemskerk, J., Korzh, V., Norlin, S., Ruiz i Altaba, A., Tanabe, Y., Placzek, M., Edlund, T., Jessell, T. M. & Dodd, J. Floor plate and motor neuron induction by vhh-1, a vertebrate homolog of hedgehog expressed by the notochord. *Cell* 76, 761–775 (1994).
5. Fan, C.-M., Porter, J. A., Chiang, C., Chang, D. T., Beachy, P. A. & Tessier-Lavigne, M. Long-range sclerotome induction by sonic hedghehog: direct role of the amino terminal cleavage product and modulation by the cyclic AMP signaling pathway. *Cell* 81, 457–465 (1995).
6. Hynes, M., Porter, J. A., Chiang, C., Chang, D., Tessier-Lavigne, M., Beachy, P. A. & Rosenthal, A. Induction of midbrain dopaminergic neurons by sonic hedgehog. *Neuron* 15, 35–34 (1995).
7. Concordet, J.-P., Lewis, K. E., Moore, J., Goodrich, L. V., Johnson, R. L., Scott, M. P. & Ingham, P. W. Spatial regulation of a zebrafish patched homologue reflects the roles of sonic hedgehog and protein kinase A in neural tube and somite patterning. *Development* 122, 2835–2846 (1996).
8. Epstein, D. J., Marti, E., Scott, M. P. & McMahon, A. P. Antagonizing cAMP dependent protein kinase A in the dorsal CNS activates a conserved Sonic hedgehog signaling pathway. *Development* 122, 2885–2894 (1996).
9. Goodrich, L. V. Johnson, R. L., Milenkovic, L., McMahon, J. A. & Scott, M. P. Conservation of the hedgehog/patched signaling pathway from flies to mice: induction of a mouse patched gene by hedgehog. *Genes Dev.* 10, 301–312 (1996).
10. Hammerschmidt M., Bitgood, M. J. & McMahon, A. P. Protein kinase A is a common negative regulator of hedgehog signaling in the vertebrate embryo. *Genes and Dev.* 10, 647–658 (1996).
11. Marigo, V., Johnson, R. L., Vortkamp, A. & Tabin, C. J. Sonic hedgehog differentially regulates expression of Gli and Gli3 during limb development. *Dev. Biol.* 180, 273–283 (1996).
12. Stone, D. M., Hynes, M., Armanini, M., Swanson, T. A., Gu, Q., Johnson, R. L., Scott, M. P., Pennica, D., Goddard, A., Phillips, H., Noll, M., Hooper, J. E., de Sauvage, F. & Rosenthal, A. The tumor suppressor gene patched encodes a candidate receptor for sonic hedgehog. *Nature* 384, 129–134 (1996).
13. Lee, J., Platt, K. A., Censullo, P. & Ruiz i Altaba, A. Gli1 is a target of sonic hedgehog that induces ventral neural tube development. Development in press (1997).
14. Kinzler, K. W., Bigner, S. H., Bigner, D. D., Trent, J. M., Law, M. L., O'Brien, S. J., Wong, A. J. & Vogelstin, B. Identification of an amplified, highly expressed gene in a human glioma. *Science* 236, 70–73 (1987).
15. Ruppert, J. M., Vogelstein, B. & Kinzler, K. W. The zinc finger protein GLI transforms primary cells in cooperation with adenovirus E1A. *Molecular and Cellular Biology* 11, 1724–1728 (1991).
16. Ruppert, J. M., Vogelstein, B., Arheden, K. & Kinzler, K. W. GLI3 encodes a 190 kilodalton protein with multiple regions of GLI similarity. *Mol. Cell Biol.* 10, 5408–5415 (1990).
17. Hui, C.-C., Slusarski, D., Platt, K. A., Holmgren, R. & Joyner, A. L. Expression of three mouse homologs of the Drosophila segment polarity gene cubitus interruptus, Gli, Gli2 and Gli3 in ectoderm and mesoderm-derived tissues suggests multiple roles during postimplantation development. *Developmental Biology* 162, 402–413 (1994).
18. Forbes, A. J., Nakano, Y., Taylor, A. M. & Ingham, P. W. Genetic analysis of hedgehog signalling in the Drosophila embryo. *Development Supplement* 115–124 (1993).
19. Dominguez, M., Brunner, M., Hafen, E. & Basler, K. Sending and receiving the hedgehog signal: control by the Drosophila Gli protein cubitus interruptus. *Science* 272, 1621–1625 (1996).
20. Alexandre, C., Jacinto, A. & Ingham, P. W. Transcriptional activation of hedgehog target genes in Drosophila is mediated directly by the cubitus interruptus protein, a 20. member of the GLI family of zinc finger DNA-binding proteins. *Genes and Dev.* 10, 2003–2013 (1996).
21. Hepker, J., Wang, Q.-T., Motzny, C. K., Holmgren, R. & Orenic, T. V. Drosophila cubitus interruptus forms a negative feedback loop with patched and regulates expression of hedgehog target genes. *Development* 124, 549–558 (1997).
22. von Ohnen, T., Lessing, D., Nusse, R. & Hooper, J. E. Hedgehog signaling regulates transcription through cubitus interruptus, a sequence-specific DNA binding protein. *Proc. Natl. Acad. Sci. USA*. 94, 2404–2409 (1997).
23. Mullor, J. L., Calleja, M., Capdevila, J. & Guerrero, I. Hedgehog activity, independent of Decapentaplegic, participates in wing disc patterning. *Development* 124, 1227–1237 (1997).
24. Marti, E., Bumcrot, D. A., Takada, R. & McMahon, A. P. Requirement of 19K form of Sonic hedgehog for induction of distinct ventral cell types in CNS explants. *Nature* 375, 322–325 (1995).
25. Ruiz i Altaba, A., Roelink, H. & Jessell, T. M. Restrictions to Floor Plate Induction by hedgehog and Winged Helix Genes in the Neural Tube of Frog Embryos. *Mol. Cell. Neurosci.* 6, 106–121 (1995).
26. Chiang, C., Litingtung, Y., Lee, E., Young, K. E., Corden, J. L., Westphal, H. & Beachy, P. A. Cyclopia and defective axial patterning in mice lacking Sonic hedgehog gene function. *Nature* 383, 407–413 (1996).
27. Ericson, J., Morton, S., Kawakami, A., Roelink, H. & Jessell, T. M. Two critical periods of sonic hedgehog signaling required for the specification of motor neuron identity. *Cell* 87, 661–673 (1996).
28. Ruiz i Altaba, A., Cox, C., Jessell, T. & Klar, A. Deregulated Expression of the Midline Transcription Factor Pintallavis Induces Ectopic Expression of a Floor Plate Marker. *Proc. Natl. Acad. Sci. USA* 90, 8268–8272 (1993).
29. Ruiz i Altaba, A., Prezioso, V. R., Darnell, J. E. & Jessell, T. M. Sequential expression of HNF-3β and HNF-3α by embryonic organizing centers: the dorsal lip/node, notochord and floor plate. *Mech. Dev.* 44, 91–108 (1993).
30. Hahn, H., Wicking, C., Zaphiropoulos, P. G., Gailani, M. R., Shanley, S., Chidambaram, A., Vorechovsky, I., Holmberg, E., Unden, A. B., Gillies, S., Negus, K., Smyth, I., Pressman, C., Leffell, D. J., Gerrard, B., Goldstein, A. M., Dean, M., Toftgard, R., Chenevix-Trench, G., Wainwright, B. & Bale, A. E. Mutations of the Human Homolog of Drosophila patched in the Nevoid Basal Cell Carcinoma Syndrome. *Cell* 85, 841–851 (1996).
31. Johnson, R. L., Rothman, A. L., Xie, J., Goodrich, L. V., Bare, J. W., Bonifas, J. M., Quinn, A. G., Myers, R. M., Cox, D. R., Epstein, E. H., Jr. & Scott, M. P. Human Homolog of patched, a Candidate Gene for the Basal Cell Nevus Syndrome. *Science* 272, 1668–1671 (1996).
32. Gailani, M. R., Stähle-Bäckdahl, M., Leffell, D. J., Glynn, M., Zaphiropoulos, P. G., Pressman, C., Unden, A. B., Dean, M., Brash, D. E., Bale, A. E. & Toftgärd, R. The role of the human homologue of the Drosophila patched in sporadic basal cell carcinomas. *Nature Genet.* 14, 78–81 (1996).
33. Bryne, C., Tainsky, M. & Fuchs, E. Programming Gene Expression in Developing Epidermis. *Development* 120, 2369–2383 (1994).
34. Chen, Y. & Struhl, G. Dual Roles for Patched in Sequestering and Transducing Hedgehog. *Cell* 87, 553–563 (1996).
35. Marigo, V. & Tabin, C. J. Regulation of Patched by Sonic hedgehog in the developing neural tube. *Proc. Natl. Acad. Sci. USA* 93, 9346–9351 (1996).
36. Platt, K. A., Michaud, J. & Joyner, A. L. Expression of the mouse Gli and Ptc genes is adjacent to embryonic sources of hedgehog signals suggesting a conservation of pathways between flies and mice. *Mech. Dev.* in press (1997).
37. Grimwood, R. E., Ferris, C. F., Mercill, D. B. & Huff, J. C. Expression of the mouse Gli and Ptc genes is adjacent to embryonic sources of hedgehog signals suggesting a conservation of pathways between flies and mice. *Society for Invest. Derm.* 86, 191–194 (1986).
38. Kinzler, K. W. & Vogelstein, B. The GLI gene encodes a nuclear protein which binds specific sequences in the human genome. *Mol. Cell Biol.* 10, 634–642 (1990).
39. Kelsey-Motzny. C. & Holmgren. R. The Drosophila cubitus interruptus proten and its role in the wingless and hedgehog signal transduction pathways. *Mechanisms of Development* 52, 137–150 (1995).
40. Belloni, E., Muenke, M., Roessler, E., Traverso, G., Siegel-Bartlet, J., Frumkin, A., Mitchell, H. F., Donis-Keller, H., Helms, C., Hing, A. V., Heng, H. H. Q., Koop, B., Martindale, D., Rommens, J. M., Tsui, L.-C. & Scherer, S. W. Identification of Sonic hedgehog as a candidate gene responsible for holoprosencephaly. *Nature Genetics* 14, 353–356 (1996).
41. Roessler, E., Belloni, E., Gaudenz, K., Jay, P., Berta, P., Scherer, S. W., Tsui, L.-C. & Muenke, M. Mutations in the human Sonic hedgehog gene cause holoprosencephaly. *Nature Genetics* 14, 357–360 (1996).
42. Lai, C.-L., Ekker, S. C., Beachy, P. A. & Moon, R. T. Patterning of the neural ectoderm of Xenopus laevis by the amino-terminal product of hedgehog autoproteolytic cleavage. *Development* 121, 2349–2360 (1995).
43. Ekker, S. C., McGrew, L. L., Lai, C.-J., Lee, J. J., von Kessler, D. P., Moon, R. T. & Beachy, P. A. Distinct expression and shared activities of members of the hedgehog gene family of Xenopus laevis. *Development* 121, 2337–2347 (1995).
44. Walterhouse, D. Ahmed, M., Slusarski, D., Kalamaras, J., Boucher. D., Holmgren, R. & lannaccone, P. Gli, a zinc finger trasncription factor and oncogene, is expressed during normal mouse development. *Developental Dyn.* 196, 91–102 (1993).
45. Iseki, S., Araga, A., Ohuchi, H., Nohno, T., Yoshioka, H., Hayashi, F. & Noji, S. Sonic hedgehog is expressed in epithelial cells during development of whisker, hair, and tooth. *Biochem. Biophys. Res. Commun.* 218, 688–693 (1996).
46. Bitgood, M. J. & McMahon, A. P. Hedgehog and Bmp genes are coexpressed at many diverse sites of cell-cell interaction in the mouse embryo. *Dev. Biol.* 172, 126–138 (1996).
47. Nohno, T., Kawakami, Y., Ohuchi, H., Fujiwara, A., Yoshioka, H. & Noji, S.Biochem and Involvement of the Sonic Hedgehog Gene in Chick Feather Formation. *Biophys Res Comm.* 206, 33–39 (1995).
48. van der Schroeff, J. G., Evers, L. M., Boot, A. J. M. & Box, J. L. Ras Oncogene Mutations in Basal Cell Carcinomas and Squamous Cell Carcinomas of Human Skin. Aberrant bcl-2 Protein Expression provides a possible Mechanism of Neoplastic Cell Growth in Cutaneous Basal-Cell Carcinoma. *Society for Invest Derm* 94, 423–425 (1990).
49. Cerroni, L. & Kerl, H. Aberrant bcl-2 Protein Expression provides a possible Mechanism of Neoplastic Cell Growth in Cutaneous Basal-Cell Carcinoma. *J Cutan Pathol* 21, 398–403 (1994).
50. Roberts, W. M., Douglass, E. C., Peiper, S. C., Houghton, P. J. & Look, A. T. Amplification of the gli Gene in Childhood Sarcomas. *Cancer Research* 49, 5407–5413 (1989).
51. Salgaller, M., Pearl, D. & Stephens, R. In situ hybridization with single-stranded RNA probes to demonstrate infrequently elevated gli mRNA and no increased ras mRNA levels in meningiomas and astrocytomas. *Cancer Letters* 57, 243–253 (1991).
52. Fuller, G. N. & Bigner, S. H. Amplified Cellular Oncogenes in Neoplasms of the Human Central Nervous System. *Mutation Research* 276, 299–306 (1992).
53. Xiao, H., Goldthwait, D. A. & Mapstone, T. A Search for Gli Expression in Tumors of the Central Nervous System. *Pediatr Neurosurg* 20, 178–182 (1994).
54. Cotsarelis, G., Sun, T.-T. & Lavker, R. M. Label-retaining cells reside in the bulge area of pilosebaceous unit: implications for follicular stem cells, hair cylce, and skin carcinogenesis. *Cell* 61, 1329–1337 (1990).
55. Blessing, M., Nanney, L. B., King, L. E., Jones, C. M. & Hogan, B. L. M. Transgenic mice as a model to study the role of TGF-β-related molecules in hair follicles. *Genes Dev.* 7, 204–215 (1993).
56. Liem, K., Tremml, G., Roelink, H. & Jessell, T. M. Dorsal differentiation of neural plate cells induced by BMP-mediated signals from epidermal ectoderm. *Cell* 82, 969–979 (1995).
57. Wilson, P. & Hemmati-Brivanlou, A. Induction of epidermis and inhibition of neural fate by BMP4. *Nature* 376, 331–333 (1995).
58. Wallace, S. A. & Halpert, B. Trichoma: tumor of hair anlage. *Arch. Pathol* 50, 199 (1950).
59. Elder, D. Ed. in chief. *Lever's Histopatology of the Skin.* 8th Edition. Philadelphia, Lippincott-Raven (1997).
60. Ackerman, A. B., DeViragh, P. A. & Chongchitnant, N. *Neoplasms with follicular differentiation.* Phildephia: Lea and Febinger. Phildephia: Lea and Febinger (1993).
61. Shimizu, N. Ito, M, Tazawa, T et at., Anti-keratin monoclonal antibody against basal cell epithelioma keratin: BKN-1. *J. Dermatol* 14, 359–363 (1987).
62. Urano, Y., Asano, T., Yoshimoto, K., Iwahana, H., Kubo, Y., Kato, S., Sasaki, H., Takeuchi, N., Uchida, N., Nakanishi, H., Arase, S. & Itakura, M. Frequent $p^{53}$ Accumulation in the Chronically Sun-Exposed Epidermis and Clonal Expansion of $p^{53}$ Mutant Cells in the Epidermis Adjacent to Basal Cell Carcinoma. *Society for Invest. Derm.* 104, 928–932 (1995).
63. Ruiz i Altaba, A. *In Essential Developmental Biology—A Practical Approach.* (C. Stern and P. W. H. Holland) IRL Press, Oxford (1993).
64. Scharen-Wiemers, N. & Gerlin-Moser, A. A single protocol to detect transcripts of various types and expression levels in neural tissue and cultures cells: in situ hybridization using digoxygenin-labeled cRNA probes. *Histochemistry* 100, 431–440 (1993).

What is claimed is:

1. A method for detection of the onset or presence of sporadic basal cell carcinoma in an animal, said method comprising provided a skin sample from said animal suspected of harboring sporadic basal cell carcinoma, measuring the level of Gli1 in said sample, and detecting the presence or onset of sporadic basal cell carcinoma based on said measurement of Gli1, wherein elevated levels of Gli1 above normal indicate said presence or onset of sporadic basal cell carcinoma.

2. A method for detection of the onset or presence of sporadic basal cell carcinoma in an animal, said method comprising providing a skin sample from said animal suspected of harboring sporadic basal cell carcinoma, culturing said sample with either a frog embryo or a test cell colony, said culturing being for a time sufficient for development of skin tumors on said frog embryo or tumor formation in said test colony if said sample contains elevated levels of ectopically expressed Gli1 above normal, and examining said frog embryo for skin tumors or said test cell colony for tumor formation, wherein development of frog embryo skin tumors or test cell colony tumor formation is indicative of the presence or onset of sporadic basal cell carcinoma.

* * * * *